United States Patent
Bachalo (10) Patent No.: US 7,126,694 B1
(45) Date of Patent: Oct. 24, 2006

(54) COMPACT APPARATUS PROVIDING MULTI-DIMENSIONAL CHARACTERIZATION OF SPHERICAL OBJECTS USING COHERENT LIGHT

(75) Inventor: William D. Bachalo, Los Altos Hills, CA (US)

(73) Assignee: Artium Technologies, Inc., Sunnyvale, CA (US)

( * ) Notice: Subject to any disclaimer, the term of this patent is extended or adjusted under 35 U.S.C. 154(b) by 0 days.

(21) Appl. No.: 10/846,402

(22) Filed: May 14, 2004

(51) Int. Cl.
G01B 9/02 (2006.01)

(52) U.S. Cl. ............... 356/484; 356/336; 356/28.5

(58) Field of Classification Search ............. 356/28.5, 356/484, 486, 493, 498
See application file for complete search history.

(56) References Cited

U.S. PATENT DOCUMENTS

| | | | |
|---|---|---|---|
| 3,966,324 A * | 6/1976 | Iten | 356/28.5 |
| 4,329,054 A | 5/1982 | Bachalo | |
| 4,540,283 A * | 9/1985 | Bachalo | 356/336 |
| 4,697,922 A * | 10/1987 | Gunter et al. | 356/28.5 |
| 4,807,990 A * | 2/1989 | Keefer | 356/28.5 |
| 4,838,687 A * | 6/1989 | Pfeifer | 356/28.5 |
| 4,854,705 A | 8/1989 | Bachalo | |
| 4,986,659 A | 1/1991 | Bachalo | |
| 5,289,391 A | 2/1994 | Ibrahim et al. | |
| 5,808,895 A | 9/1998 | Ibrahim et al. | |
| 6,654,102 B1 * | 11/2003 | Modares et al. | 356/28.5 |

OTHER PUBLICATIONS

S.V. Sankar, et al., "Performance Analysis of Various Phase Doppler Systems," presented at 4th International Congress on Optical Particle Sizing, Nuremberg, Germany (Mar. 21-23, 1995).

Peter A. Strakey, et al., "Phase-Doppler Interferometry with Probe-to-Droplet Size Ratios Less Than Unity I. Trajectory Errors," Applied Optics, vol. 39, No. 22, pp. 3875-3886 (Aug. 1, 2000).

Peter A. Strakey, et al., "Phase-Doppler Interferometry with Probe-to-Droplet Size Ratios Less Than Unity II. Application of the Technique," Applied Optics, vol. 39, No. 22, pp. 3887-33893 (Aug. 1, 2000).

W.D. Bachalo, et al., "Development of the Phase/Doppler Spray Analyzer for Liquid Drop Size and Velocity Characterizations," AIAA/SAE/ASME 20th Joint Propulsion Conference, Cincinnati, Ohio, American Institute of Aeronautics and Astronautics, New York, pp. 1-13 (Jun. 11-13, 1984).

(Continued)

Primary Examiner—Layla G. Lauchman
Assistant Examiner—Denise B Anderson
(74) Attorney, Agent, or Firm—Blakely, Sokoloff, Taylor & Zafman LLP (57) ABSTRACT

A compact computer-controlled fully-packaged apparatus providing reliable multi-dimensional characterization of spherical objects in a field environment is disclosed. The apparatus has a rugged, free-space, integrated optical system with up to three lasers that generate at a laser-specific wavelength the coherent light with substantially high pointing stability. The apparatus also has a receiver. Each laser generates a pair of beams crossing each other at a predetermined laser specific angle to form a sample volume such that beams from all lasers coincide in the same spot. The receiver has photodetectors to sense the light scattered from a spherical object. Three photodetectors measure a size and one of the three photodetectors measures a first velocity component, a fourth photodetector measures a second velocity component, and a fifth photodetector measures a third velocity component of the spherical object. The velocity components are orthogonal to each other.

21 Claims, 10 Drawing Sheets

OTHER PUBLICATIONS

W.D. Bachalo et al., "Phase/Doppler Spray Analyzer for Simultaneous Measurements of Drop Size and Velocity Distributions," Optical Engineering, vol. 23, No. 5, pp. 583-590 (Sep./Oct. 1984).

W.D. Bachalo, et al., "Method for measuring the size and velocity of Spheres by Dual-Beam Light-Scatter Interferometry," Applied Optics, vol. 19, No. 3, pp. 363-370 (Feb. 1, 1980).

W.D. Bachalo and S.V. Sankar, "5.0 Phase Doppler Particle Analyzer (PDPA)," a chapter from "A Handbook of Fluid Dynamics" by R.W. Johnson, CRC Press (Washington, D.C. 1998).

CrystaLaser product information document, 7 pgs. (dated prior to May 14, 2004).

* cited by examiner

COMPACT APPARATUS PROVIDING MULTI-DIMENSIONAL CHARACTERIZATION OF SPHERICAL OBJECTS USING COHERENT LIGHT

FIELD

Embodiments of the invention relate to devices to characterize spherical objects, including particles, droplets, bubbles, and the like. More particularly, embodiments of the invention relate to a stable, compact, computer-controlled apparatus that provides reliable multi-dimensional characterization of spherical particles, droplets, bubbles, and the like, in various environments.

BACKGROUND

Information on size and velocity of spherical objects including particles, droplets, bubbles, etc., is important for numerous applications in various industries. These applications include, for example, fuel spray combustion analysis and control for the automotive industry, inhaler manufacturing for the pharmaceutical industry, household spray manufacturing, agricultural pesticide irrigation, aircraft icing analysis and control, spray nozzle manufacturing, atmospheric aerosol analysis, and various combustion related applications.

Normally, a laser light scattering interferometry technique is used to determine the size and velocity of spherical objects, such as particles, drops, bubbles, etc. According to this technique, spherical objects under the test pass the intersection point of two crossed laser beams generated from the same laser. The light scattered from the spherical object, as it passes the intersection point of two laser beams, forms a fringe pattern on the detector. The spatial period of the interference fringe pattern generated by the spherical object, as it passes through the intersection point of two crossed laser beams, is used to determine the particle size and one velocity component in the plane of two crossing laser beams. In order to obtain a reliable and accurate measurement, it is important to provide a stable interference pattern on the detector. The shape and spacing of the fringes formed by the scattered light depend on the angle between the incident laser beams, their wavelength, the direction of the light collection, and the particle diameter. In particular, the quality of the interference pattern on the detector depends on the pointing stability of two crossing beams and on the coherence length of the laser. For example, a longer coherence length of a laser provides a better quality interference pattern. Further, to obtain a substantially high signal-to-noise ratio of the signal generated from the scattered light, the probing laser needs to output enough optical power to compensate for losses in the optical system.

Certain prior art light scattering interferometry optical systems use a gas laser. A gas laser, however, typically is bulky, consumes a lot of electrical power, and requires a cooling system involving water or forced air. Accordingly, optical systems that use such lasers are typically bulky and sophisticated. Such systems usually consume a lot of electrical power and involve frequent realignment to ensure measurement reliability and accuracy. Highly skilled professionals are usually required to operate such systems. Such prior art systems typically do not reside in a single compact, portable package. Such prior art systems are typically not used for daily testing and quality control in highly-paced manufacturing and field environments.

Other light scattering interferometry prior art optical systems used to measure particle size and a velocity component employ a solid-state laser. The output of the solid-state laser is coupled to a polarization-preserving single-mode optical fiber to direct two crossing laser beams onto the spherical particle under the test. In such prior art systems, the light scattered from the particle is collected into the multi-mode optical fiber that brings the scattered light to photodetectors to measure the scattered light signal.

Figure 1:
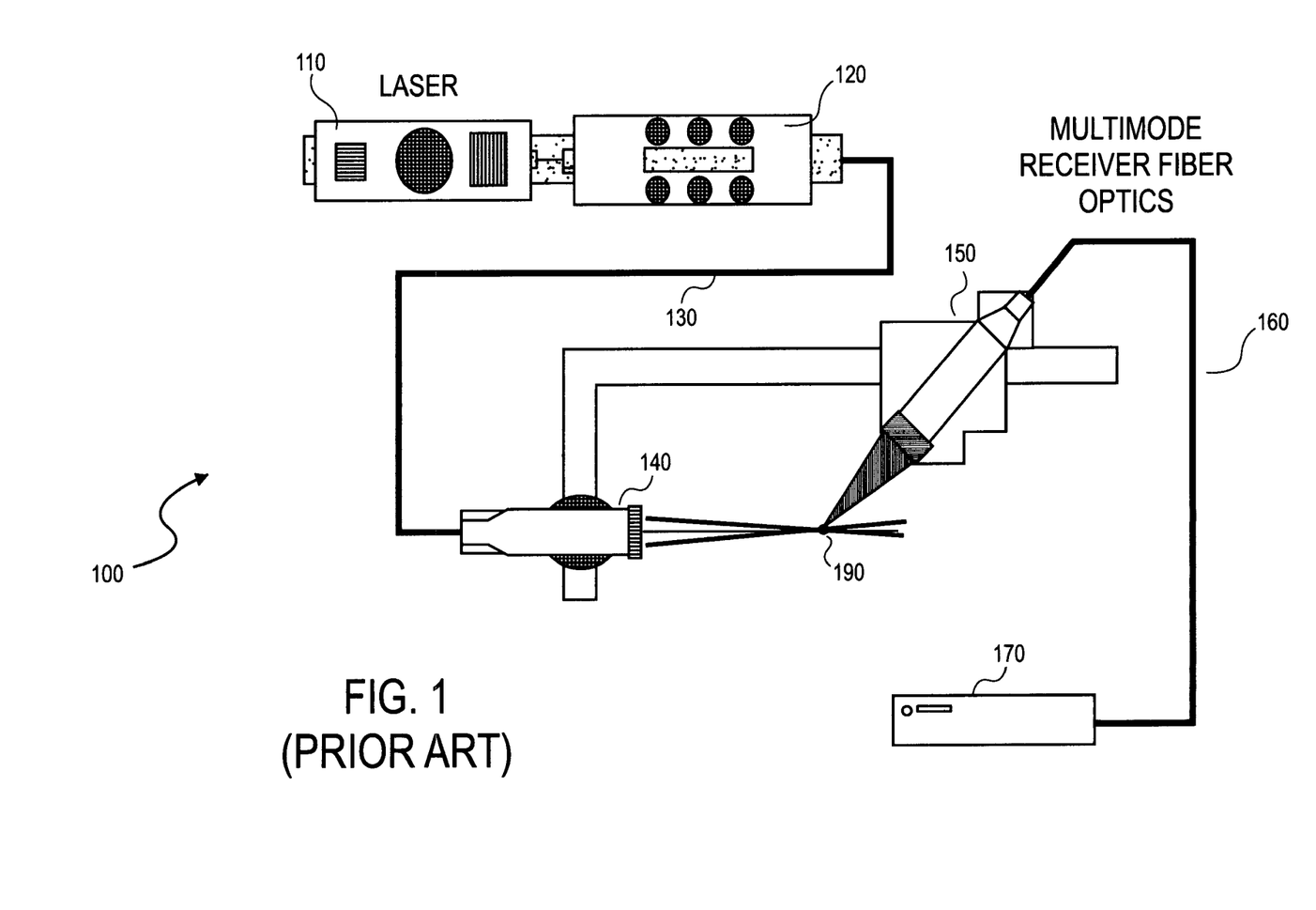
FIG. 1 shows a prior art optical system for phase Doppler interferometer measurements using single-mode polarization-preserving fibers and multimode fiber optics for receiving the scattered light.

FIG. 1 is an illustration of a prior art optical system using a gas (He—Ne or Argon) or solid-state laser. The laser has the output light coupled into single-mode polarization preserving fibers to direct two crossing beams onto the particle. Multimode fiber optics receive the scattered light from the particle. As shown in FIG. 1, the output of the laser 110 is connected through the coupler component 120 to a single mode polarization preserving fiber 130. The optical fiber output head 140 is positioned on the rail to direct crossing beams onto the particle 190. The scattered light from the particle is collected by the input head 150 of a multimode fiber, which is positioned on the rail at a predetermined angle relative to the incident light, and directed by the multimode fiber 160 to the receiver module 170. The signal from the receiver module 170 may further be processed by a signal processor to obtain the information on the size and velocity component of the particle.

The use of movable, fragile optical fibers can, however, put the stability of the optical alignment of the system at risk. In particular, the alignment of the laser beam to a single mode polarization preserving fiber having a small fiber diameter from 2 to 5 micrometers ("um") is crucial to the stability of the intersection point of incident laser beams to provide accurate and reliable measurements. In addition, losses of the laser light in the coupling at the output of the laser typically substantially reduce the overall laser efficiency, leading to higher electrical power consumption by the system. Further, losses of the scattered light from the particle in the coupling into the multimode fiber typically significantly reduce the overall sensitivity of the receiver, leading to the system's substantially reduced operating range. Furthermore, typically time-consuming high-precision assembly of such optical systems is required to couple the light into the optical fiber.

SUMMARY

An apparatus is described having a compact package. A first transmitter inside the compact package generates a first pair of coherent beams with a substantially high pointing stability. The coherent beams of the first pair are guided by a free space optics inside the package along a first axis and cross each other outside the package at a first angle in a first plane to form a sample volume to illuminate a spherical object outside the package. A receiver inside the compact package senses a first light scattered from the spherical object. The receiver comprises three photodetectors to measure a size and a first velocity component of the spherical object.

Other features and advantages of embodiments of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements, in which.

DETAILED DESCRIPTION

An apparatus for characterizing spherical objects is described in more detail below. The apparatus has a compact package that includes at least one transmitter module having a laser to generate, at a predetermined wavelength, a pair of coherent beams having substantially high pointing stability. Free-space optics guide the coherent beams to cross each other outside the compact package at a predetermined angle to form a sample volume to illuminate a spherical object outside the compact package. A frequency modulator (e.g., Bragg cell) is coupled to the laser to modulate one of the coherent beams.

The compact package of the apparatus includes a receiver module having a collecting free-space optics to collect the light scattered from the spherical object and direct that light onto a plurality of photodetectors. The plurality of photodetectors are used to sense the scattered light and measure the frequency and phase of the scattered light using a phase Doppler interferometry technique.

The receiver module further has an electrical amplifier circuit with adjustable gain to provide an amplified electrical signal to a signal processor module. The signal processor module processes the electrical signal and obtains data on size and velocity of the spherical objects. The signal processor module is connected to a computer comprising software to control the apparatus operations. That includes automated set-up and data acquisition, processing, and storage to further process the data and obtain information, for example, on the size distribution and mean values of the spherical objects without the requirement of assuming a size distribution function of the testing spherical objects. The apparatus can compute size-velocity correlations that are useful, for example, in drop impact and deposition testing, or in studying droplet response in turbulent flow fields.

The apparatus for characterizing spherical objects uses compact, highly coherent lasers having substantially high pointing stability and rigid free-space optical alignment. Accordingly, the apparatus does not require frequent realignment and calibration for reliable operation. The apparatus may be used as a compact portable testing and quality control tool in the manufacturing and field environment.

The apparatus can include in the same compact package up to three compact lasers having substantially high pointing stability. The three lasers provide coherent light at three different wavelengths that permits reliable simultaneous measurement of a size and up to three different orthogonal velocity components of the spherical object. The apparatus allows measurement of the size of the spherical objects independent on light scattering intensity, so the attenuation and window fogging have a minimal effect on the apparatus performance, which is important for field applications.

The apparatus includes a computer-controlled, automatically-adjustable slit aperture in front of the receiver unit to provide, in real time, a sample volume size adjustment in accordance to various densities of spherical objects—for example, various density of particles in the flow. The real time sample volume adjustment may also be used to optimize the sampling characteristic—for example, to increase the signal-to-noise ratio. The fully-automated apparatus can measure in real time a particle velocity to simultaneously provide data on particle impact, volume flux, and number density determination, for example.

Figure 2:
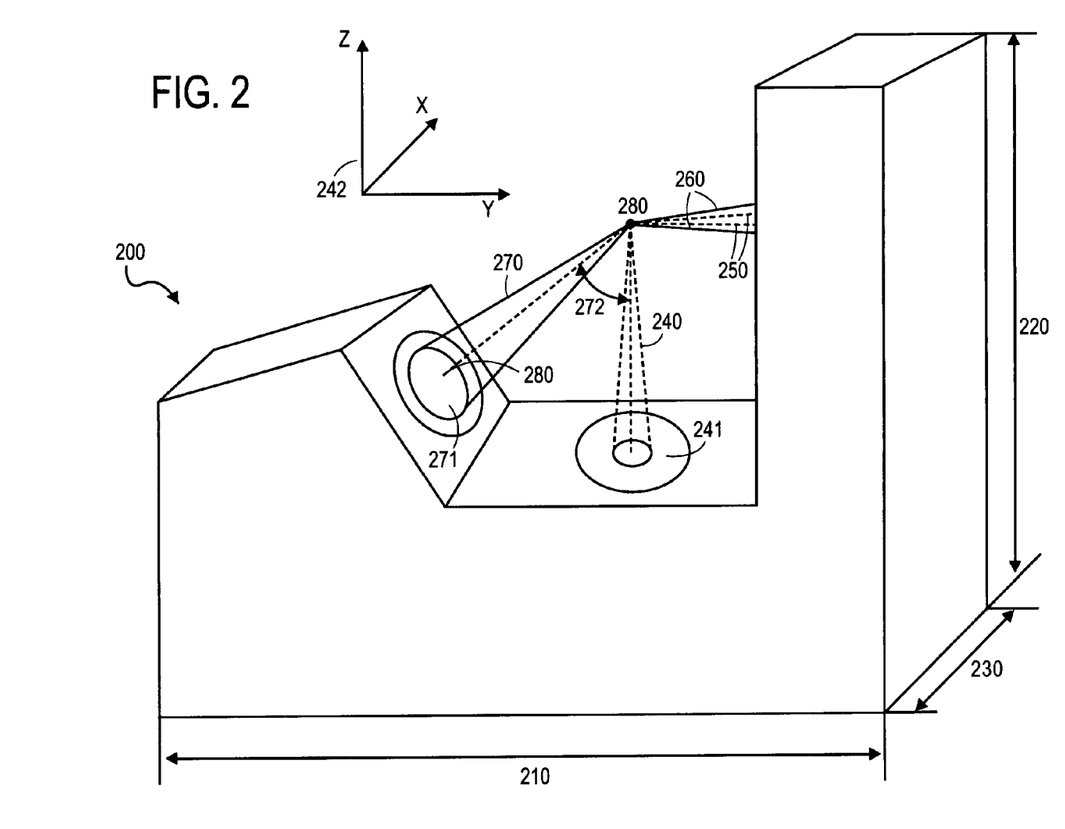
FIG. 2 is an orthogonal view of a compact-packaged apparatus to measure the size and up to three components of velocity of spherical objects according to one embodiment of the invention.

FIG. 2 is a orthogonal view of an L-shaped package of a compact fixed alignment apparatus 200 of an embodiment of the invention that can simultaneously measure a size and up to three components of velocity of spherical objects. Three pairs of highly coherent crossing beams 240, 250, and 260 originate from two openings in the package 200. The beams, having substantially high pointing stability, simultaneously form, in one spot, a sample volume to illuminate a spherical object 280. For one embodiment, the coherent length of the beams is at least about 10 meters ("m") and a pointing stability of the beams is at least about 0.02 milliradians ("mrad").

Beam propagation with respect to the Cartesian coordinate system 242 is shown in FIG. 2. The pair of beams 240 propagates along Z axis in the plane ZY to measure a velocity component along Y axis. The pair of beams 250 propagates along Y axis in the plane ZY to measure a velocity component along Z axis. The pair of beams 260 propagates along Y axis in the plane XY to measure a velocity component along X axis.

The scattered light 270 from the spherical particle 280 reaches a receiver window 271. The central axis of the receiver window 271 has an angle 272 with the central axis of the window 241. For an embodiment, the L-shaped package has a length 210 of about 91 centimeters (cm), a width 230 of about 20 cm, and a height 220 of about 60 cm. For one embodiment, the package of the apparatus 200 is made of aluminum. For alternate embodiments, the package may be made of other materials, such as stainless steel, titanium, plastic, etc.

Figure 3:
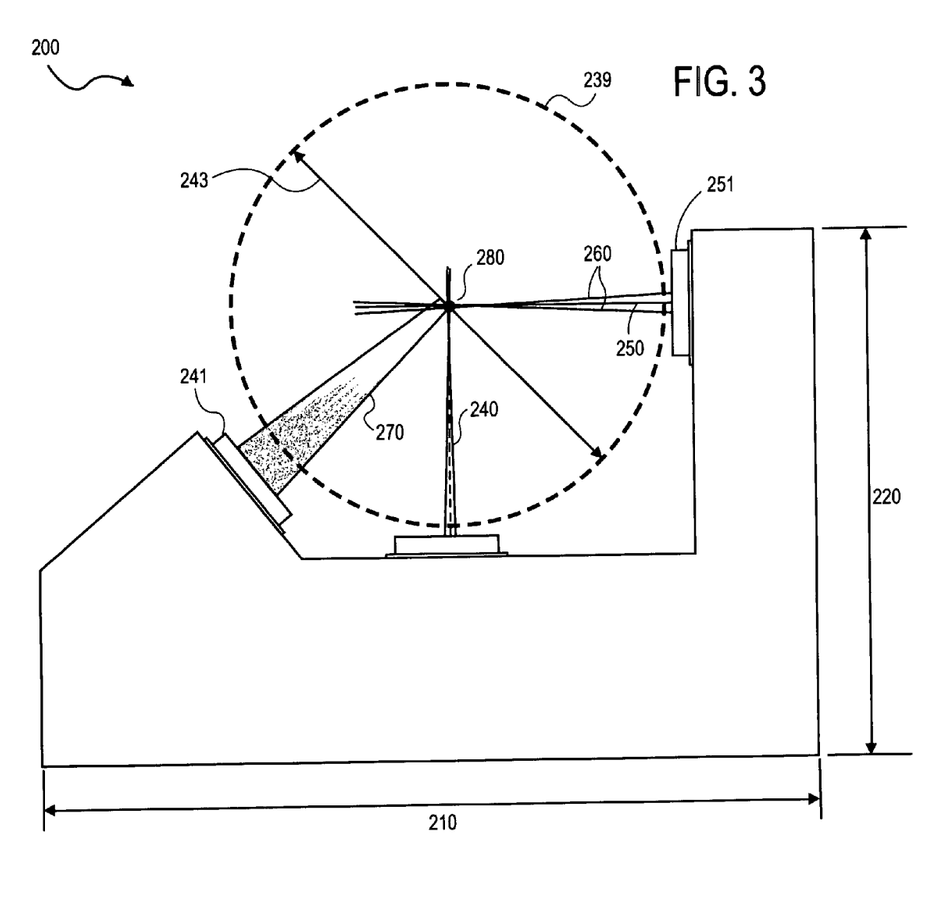
FIG. 3 is a top view of the compact packaged apparatus of FIG. 2.

FIG. 3 is a top view of the compact fixed alignment apparatus 200 having an L-shaped package. As shown in FIG. 3, the pair of beams 270 propagate from the transmitter window 241. The two pairs of beams 250 and 260 propagate from transmitter window 251. Apparatus 200 has a circular free safety area 239 with a diameter 243. The free safety area 239 is free of obstructions. If the spray under the test has a diameter 243, the spray would not interfere with the optics of apparatus 200. For one embodiment, the diameter 243 of the free area is about 500 millimeters ("mm"). For another embodiment, a hood and covers may be put on the receiver window to avoid contamination of the optics by the spray droplets.

Figure 4:
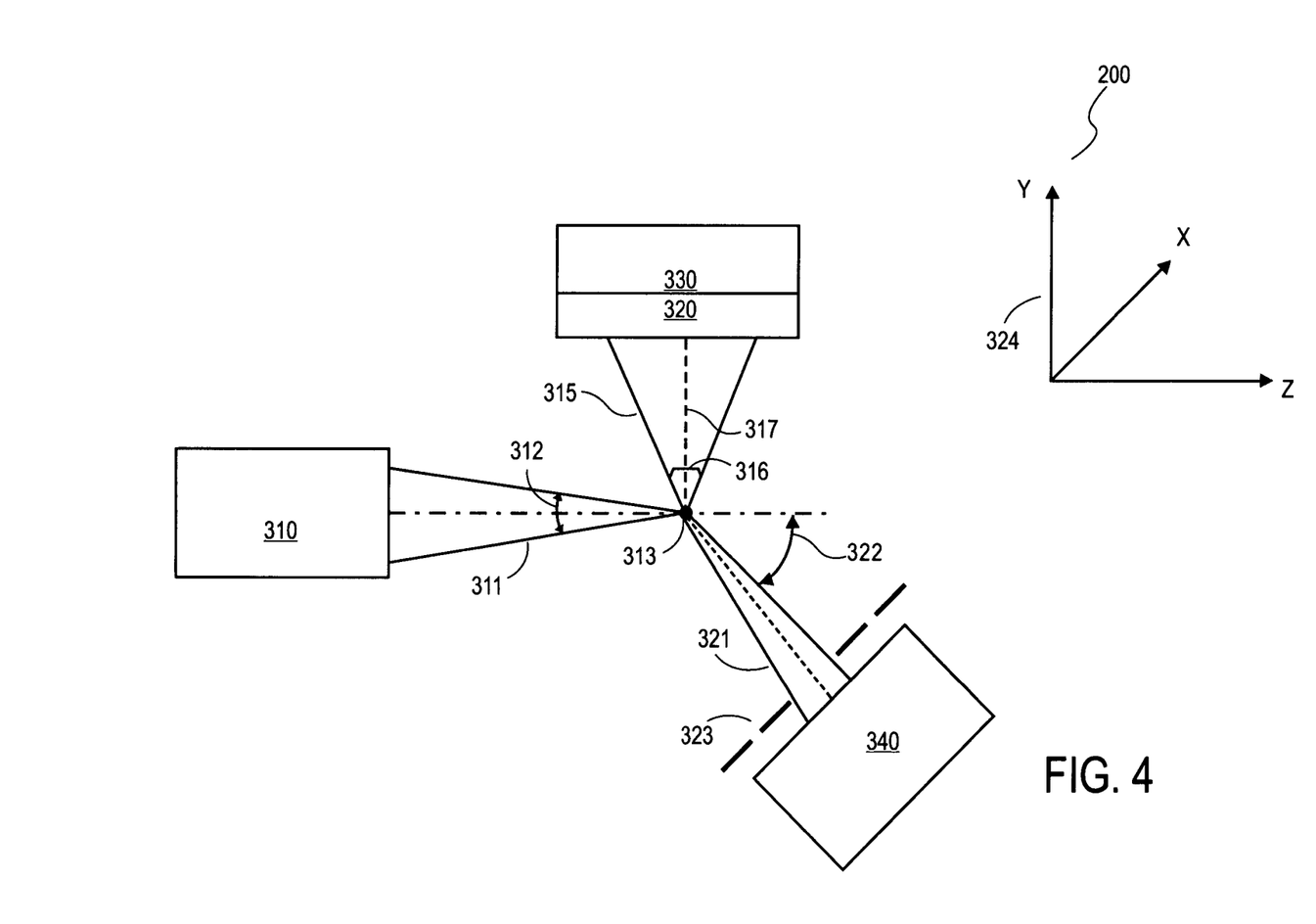
FIG. 4 is a block diagram of an apparatus of FIG. 2.

FIG. 4 is a block diagram of an apparatus 200 for measuring the size and up to three velocity components of a spherical object. Beam propagation with respect to the Cartesian coordinate system 324 is shown in FIG. 4. The apparatus 200 has a transmitter 310 for generating a pair of coherent beams 311 propagating along an axis Z in the plane ZY and crossing each other at a predetermined angle 312 to form a sample volume 313 to measure a size and an Y-velocity component of a spherical object located inside the sample volume 313. The apparatus 200 also has a transmitter 320 that generates a pair of coherent beams 315 propagating a plane ZY along an axis Y that is perpendicular to an axis Z. The beams 315 cross each other at a predetermined angle 316 to form the sample volume 313 to measure a Z-velocity component of the spherical object located inside the sample volume 313. The apparatus 200 further includes a transmitter 330 that generates a pair of coherent beams 317 propagating in a plane XY along the an axis Y. Beams 317 cross each other at a predetermined angle to form a sample volume 313 to measure an X-velocity component of the spherical object located inside the sample volume 313. For one embodiment, the transmitter 330 is stacked on top of the 320.

For an embodiment, each of the transmitters 310, 320, and 330 is a compact, highly efficient, commercially available diode-pumped solid-state ("DPSS") laser having substantially high pointing stability. For one embodiment, the DPSS laser models GCL-XXX-S, BCL-XXX-S, etc., supplied by CrystaLaser of Reno, Nev. may be used. More specifically, the pointing stability of the DPSS used in transmitters 310, 320, and 330 is less than about 0.02 mrad.

For an embodiment, to simultaneously measure the size and three velocity components of the spherical object, transmitters 310, 320, and 330 generate light at a first, a second, and a third wavelength, respectively. More specifically, the first, second, and third wavelengths are, for example, violet, red, and green, respectively. For another embodiment, each of the transmitters 310, 320, and 330 generate light having a first, second, and third polarization, respectively. For yet another embodiment, two transmitters 310 and 320 generate light having a first and second wavelength respectively, with the same polarization, and the transmitter 330 generates light having the first wavelength, but the polarization is different from the polarization of the transmitters 310 and 320.

For apparatus 200 of FIG. 4, the scattered light 321 from the spherical object is collected by a receiver unit 340 to sense the scattered light 321 and convert it to electrical signals. For an embodiment, the receiver unit 340 is positioned off-axis to the transmitter beams direction. The central axis of the receiver 340 forms a predetermined angle 322 relative to a propagation axis of the first pair of beams 311. For an embodiment, the predetermined angle 322 is in the approximate range of 25 to 45 degrees. For one embodiment, the predetermined angle 322 is about 30 degrees. The receiver 340 is in a plane that passes through the crossing of the beams, and is orthogonal to the plane formed by the two crossing beams. The apparatus 200 may also have a movable strip-like slit aperture 323 in front of the receiver unit 340. The movable strip-like aperture 323 in front of the receiver unit 340 is shown in greater detail in FIG. 5.

Figure 5:
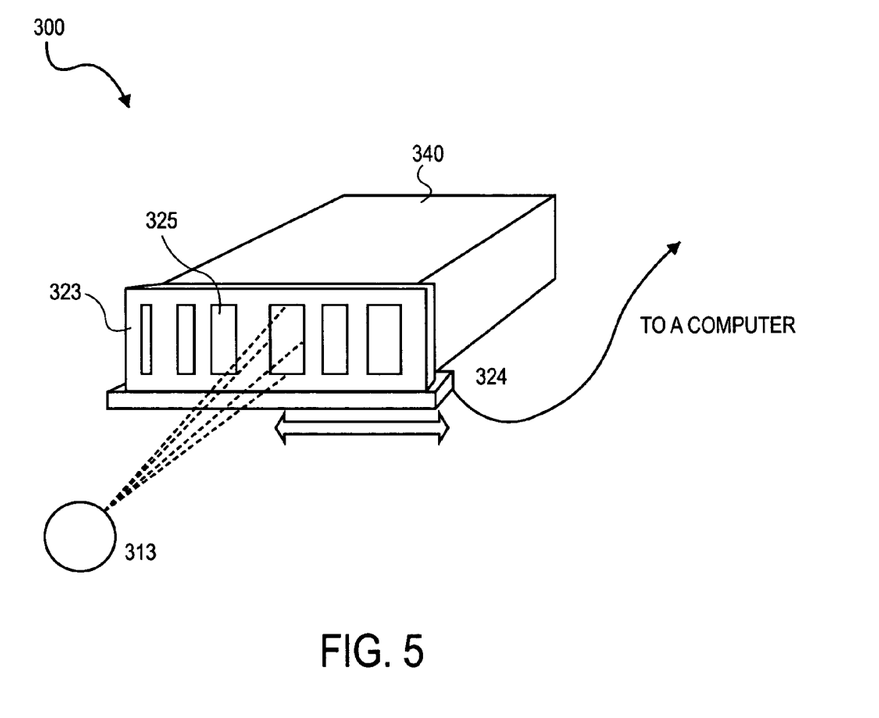
FIG. 5 is an orthogonal view of the receiver of the apparatus of FIG. 2 with a movable slit aperture.

FIG. 5 is an orthogonal view 300 of the receiver 340 of the apparatus 200 with a movable slit aperture 323. For an embodiment, the movable slit aperture 323 positioned on the motorized stage 324 has a plurality of apertures 325 of different sizes along the strip and is connected to the computer to automatically adjust aperture in front of the receiver unit 340 to adjust, in real time, sample volume size to various densities of spherical objects. The real time sample volume adjustment may also be used to optimize the sampling characteristic, for example, to increase the signal-to-noise ratio. For an alternative embodiment, the movable slit aperture may have a round shape and may rotate in front of the receiver unit 340 to adjust the aperture.

Figure 6:
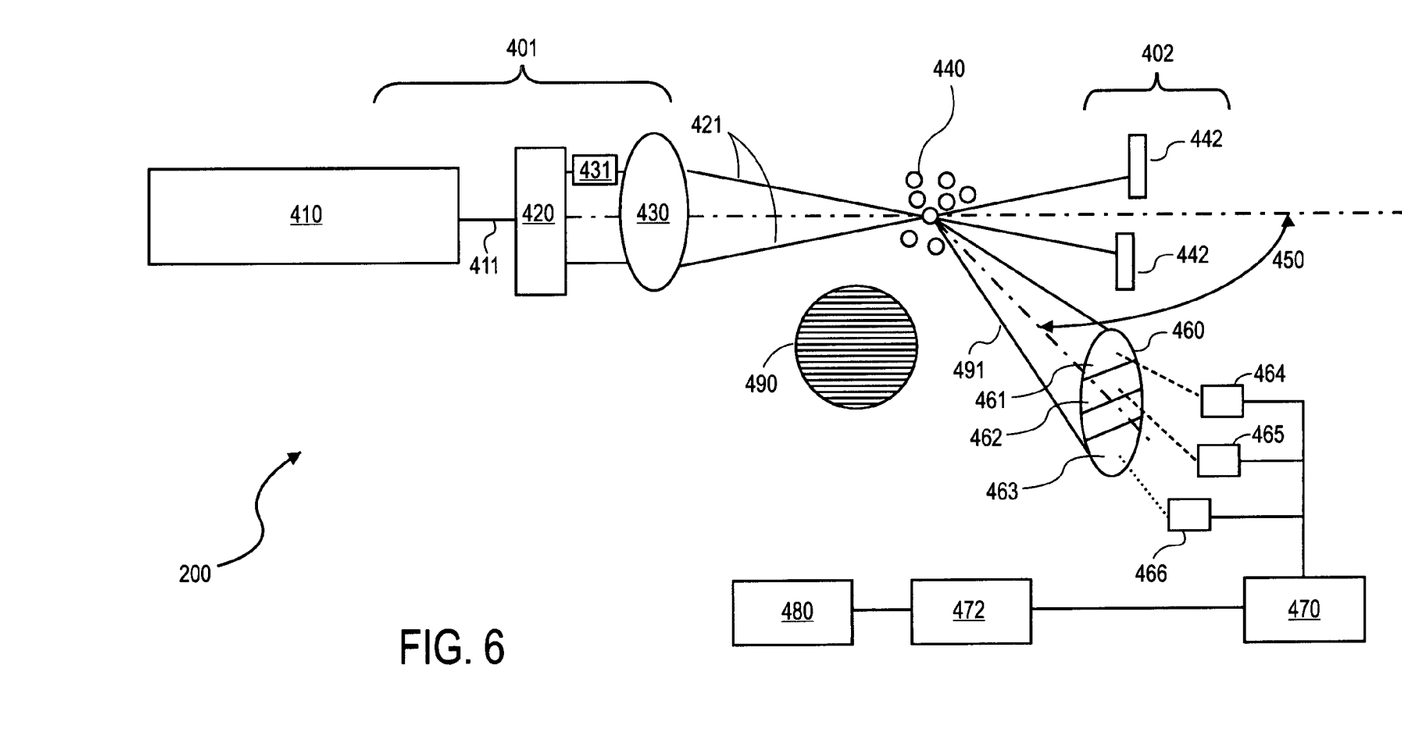
FIG. 6 shows the optical components of the apparatus of FIG. 2 of an embodiment of the invention.

FIG. 6 shows the optical components of apparatus 200 of an embodiment of the invention. Apparatus 200 has a transmitter section 401 and a receiver section 402. The transmitter section 401 includes a laser 410 that generates a laser beam 411. Laser beam 411 is further split by a beam splitter 420 into two beams 421 of equal intensity. The transmitter section 401 has a focusing optics 430 to focus the beams 421 and make them cross each other at a predetermined angle to generate an interference fringe pattern 490 and to form a sample volume. For an embodiment, the focusing optics includes a commercially available lens—for example, a glass lens.

One of the beams 421 generated by the laser is modulated with a predetermined frequency by a modulator 431 to shift the frequency up and to make the interference fringe pattern generated by crossing coherent laser beams 421 appear to be moving at a predetermined frequency to define a direction of a moving particle and to ensure a sine signal when the particle is stationary. For one embodiment, the predetermined frequency of the modulator 431 to modulate one of the laser beams 421 is 40 Megahertz ("MHz"). For an embodiment, the modulator 431 to modulate one of the laser beams 421 is an acousto-optical modulator. For one embodiment, the modulator 431 to modulate one of the laser beams 421 is a Bragg cell.

An optical receiver collecting optics 460 is positioned at a predetermined off-axis detection angle 450 from the transmitted beam direction. The light from the two crossing beams 421 is scattered by particles 440 passing through the beams' sample volume located at the beams' intersection. Further, the light scattered simultaneously from each of the two laser beams 421 interfere to form a spatially and temporally varying fringe pattern 491 on the receiver optics 461. The interference fringe pattern 491 has a sinusoidal intensity distribution and forms a hyperbolic set of curves when projected onto a receiver optics plane. The wavelength of the pattern or spacing of the interference fringes at a given location is inversely proportional to the spherical object's diameter.

The collecting optics 460 of the receiver 402 collects the scattered light, partitions it into three sections 461, 462 and 463, and directs them on to three spaced apart separate photodetectors 464, 465 and 466. Given a specific location in space (points on the receiver collecting optics' lens aperture), the phase shift between the light scattered from each of the beams 421 will vary in proportion to the spherical object's diameter. For one embodiment, the detectors 464, 465 and 466 are located in the fringe pattern, or an image of it, and the separation between the detectors is known.

When the particle or drop is moving, the usual Doppler shift in the frequency of the scattered light occurs. The difference in the Doppler frequency shift between the light scattered from each of the scattered beams 421 causes the fringe pattern to appear to move. As the pattern sweeps past the detectors at the Doppler difference frequency, each detector produces a signal that is similar in frequency but shifted in phase. The phase shift is related to the spacing of the scattered fringe pattern through the following relationship:

$$\frac{\phi}{360°} = \frac{s}{\Lambda}$$

wherein s is the detector spacing, $\phi$ is the phase shift between the signals, and $\Lambda$ is the spacing of the interference fringe pattern at that location. The wavelength $\Lambda$ is the spacing of the interference fringes formed by the scattered light and is inversely proportional to the spherical object's diameter.

Three photodetectors 464, 465, and 466 are used to provide extended size range of the spherical objects with a substantially high resolution and to produce redundant measurements to evaluate each signal in obtaining the spherical object's size. For one embodiment, the spherical object's size may be in the approximate range of 0.5 micrometers ("um") to 1000 um, for example. To measure one velocity component, any one of photodetectors 464, 465, and 466 may be used.

Three photodetectors send electrical signals to the phase measuring unit 470 to measure the phase of the scattered light that is needed to obtain the information on the particle size and velocity.

A single aperture is used in the receiver 402 to allow only light scattered by particles crossing a small region of the beam intersection to reach the photodetectors. The rest of the scattered light is blocked by light blockers 442 to minimize the noise in the signal and limit the size of the measurement volume.

Photodetectors 464, 465, and 466 send the Doppler signals to frequency and phase measuring unit 470 to measure the spatial frequency of the fringe pattern 491 and temporal frequency of the Doppler signal to obtain the particle size and one velocity component, respectively. The frequency and phase measuring unit 470 sends the signals through an electrical cable to a signal processor 472 coupled to a computer 480.

For an alternative embodiment, the signals from the frequency and phase measuring unit 470 to the signal processor 472 are sent using a wireless communication link.

For yet another embodiment, the signal processor 472 connected to the frequency and phase measuring unit 470 is incorporated into the apparatus package 200. For yet another embodiment, the computer 480 and the signal-processing unit 470 coupled to the frequency and phase measuring unit 470 are incorporated into the package of apparatus 200.

Figure 7:
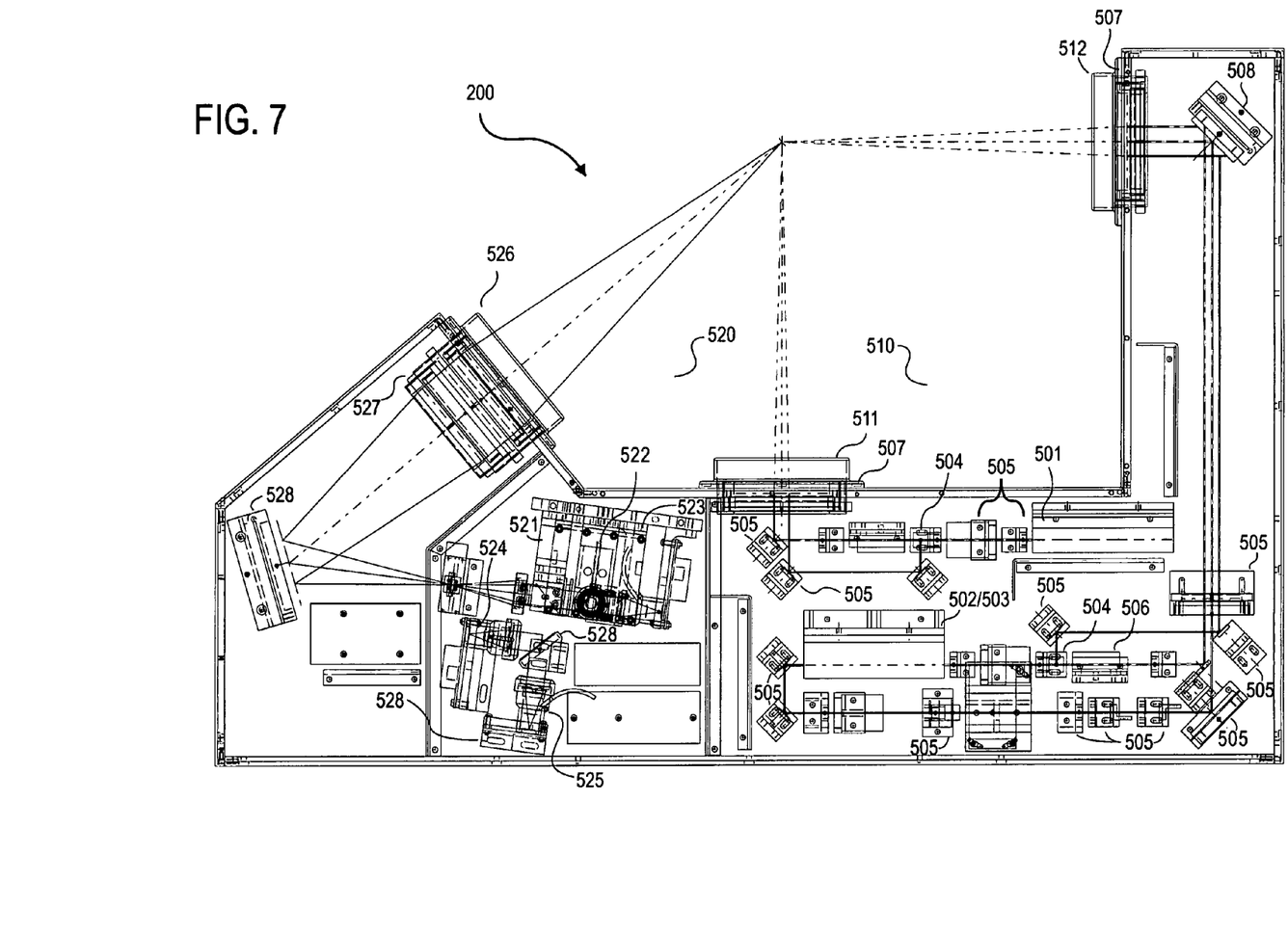
FIG. 7 is a top cross-section view of the apparatus of FIG. 2 to simultaneously measure the size and three velocity components of a spherical object.

FIG. 7 is a top cross-section view of the apparatus 200 to simultaneously measure the size and three velocity components of a spherical object. Apparatus 200 has a transmitter section 510 and a receiver section 520. The transmitter section includes a first laser 501, a second laser 502, and a third laser 503. The third laser 503 is stacked above the second laser 502. The first laser 501, the second laser 502, and the third laser 503 each generates highly coherent beams having substantially high pointing stability at a first, a second, and a third wavelength, respectively. For an embodiment, the lasers 501–503 have substantially high pointing stability, for example, not more than about 0.02 mrad. For an embodiment, the wavelength of the light generated by lasers 501–503 is not more than $10^{-5}$ nanometers ("nm"). For an embodiment, the lasers 501–503 are compact DPSS lasers that generate the output optical power in the approximate range of 200 milliwatts ("mW") to 1 Watt ("W").

The laser beam from each laser 501–503 is split by the beam splitter 504 and directed by free-space directing optics 505 and 508 to the free-space focusing optics 507 to pass through the respective transmitter windows 511 and 512. The first pair of beams is directed to the window 511 and the second and the third pairs of beams are directed to the window 512.

The free-space directing optics 505 and 508, for directing the laser beams from the lasers 501, 502 and 503 are a plurality of mirrors. Mirror 508 to direct the second and third beams to the focusing lens 507 may be factory or field adjustable to steer the beams generated from the lasers 502 and 503 with high precision and accuracy to accommodate the particle having the size beyond the range used in one optical set-up. For another embodiment, the focusing optics 507 may include a factory or field interchangeable lens to adjust the transmitter focal length to accommodate the size and density of spherical objects that are beyond the operating range available to one optical set-up. For one embodiment, the operating range available to one optical set-up is about 500:1.

Bragg cells 506 are placed at the output of each laser 501, 502, and 503 to modulate a single beam from each pair of beams. For an embodiment, the modulation frequency is about 40 MHz.

Receiver section 520 includes three spaced apart photodetectors 521, 522, and 523 to measure the size and the first velocity component of the spherical object and the photodetectors 524 and 525 to measure the second and the third velocity component of the spherical object, respectively. The scattered light is incident on the receiver window 526, collected by the free-space collecting optics 527, and directed by the plurality of mirrors 528 onto respective photodetectors 521–525, wherein the photodetectors 521–525 convert the optical signals into electrical current. The optical components of the apparatus 200, including lasers, free-space optics, and photodetectors, are pre-aligned and mounted on the rigid aluminum wall by fasteners and screws to ensure the stability of the set-up. For another embodiment, mounting is done on a rigid platform that is an aluminum plate mounted on the wall of the package. The compact package has a lid that can be removed (or opened) to gain access to the components within the package.

For an embodiment, the plurality of mirrors 528 may include dichroic mirrors to reflect light selectively according to wavelength.

For one embodiment, the free-space collecting optics may include an interchangeable lens to adjust the receiver focal length densities beyond the operating dynamic range. For an embodiment, the photodetectors 521–525 are photomultiplier tubes ("PMT") to convert optical signals into current. For another embodiment, the photodetectors 521–525 are avalanche photodetectors ("APD"). For one embodiment, a PMT's gain is automatically adjusted to accommodate various signal strengths. For another embodiment, an automatically gain adjustable transimpedance amplifier incorporated into photodetectors 521–525 is used. For an embodiment, the photodetectors 521–525 are different color detectors, meaning that they selectively sense the light according to the light's wavelength, for example, the photodetectors 521–525 sense the light at the first wavelength, the photodetector 524 senses the light at the second wavelength, and the photodetector 525 senses the light at the third wavelength, wherein the first, second, and third wavelengths are generated by the first 501, second 502, and third 503 lasers, respectively.

For an embodiment, the apparatus 200 can measure, at one optical set-up, the spherical objects having a dynamic size range of about 500:1.

For an embodiment, the apparatus 200 consumes the electrical power not more than about 10 W and is fanless. For another embodiment, the apparatus 200 is powered by a rechargeable battery. For yet another embodiment, the apparatus 200 is a portable device. For yet another embodiment, the apparatus 200 can operate in a highly combustible environment, satisfying an Occupational Safety and Health Administration ("OSHA") standard.

Figure 8:
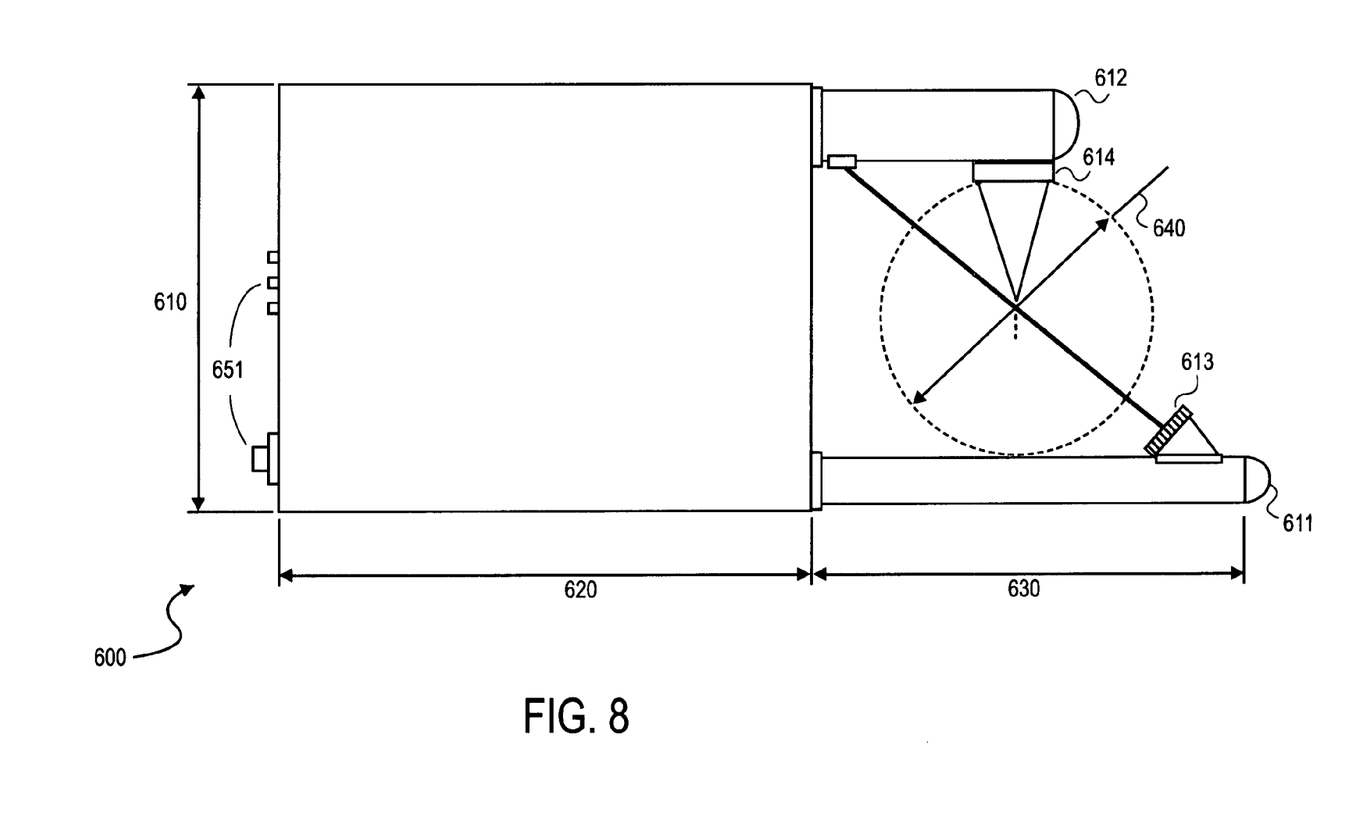
FIG. 8 is a top view of a watertight compact packaged apparatus to measure the size and one velocity component of a spherical object according to one of the embodiments of the invention.

FIG. 8 is a top view of a water tight, sealed, compact packaged apparatus 600 to measure the size and one velocity component of a spherical object according to another embodiment of the invention. The apparatus 600 includes two legs 611 and 612 having windows 613 and 614 respectively. The window 613 outputs a probe coherent light to measure the particle size, whereas the window 614 collects the scattered light from the spherical object. The apparatus includes electrical connectors 651 to output the measured electrical signal into the signal processor. The apparatus has a free safety diameter 640 defining a maximum diameter of the spray under the test allowable without obstructing the device optics. For an embodiment, the free safety area diameter 640 is about 6", length 620 of the apparatus body is about 10", width 610 of the device is about 8", and the length of the longest apparatus leg 630 is about 9".

Figure 9:
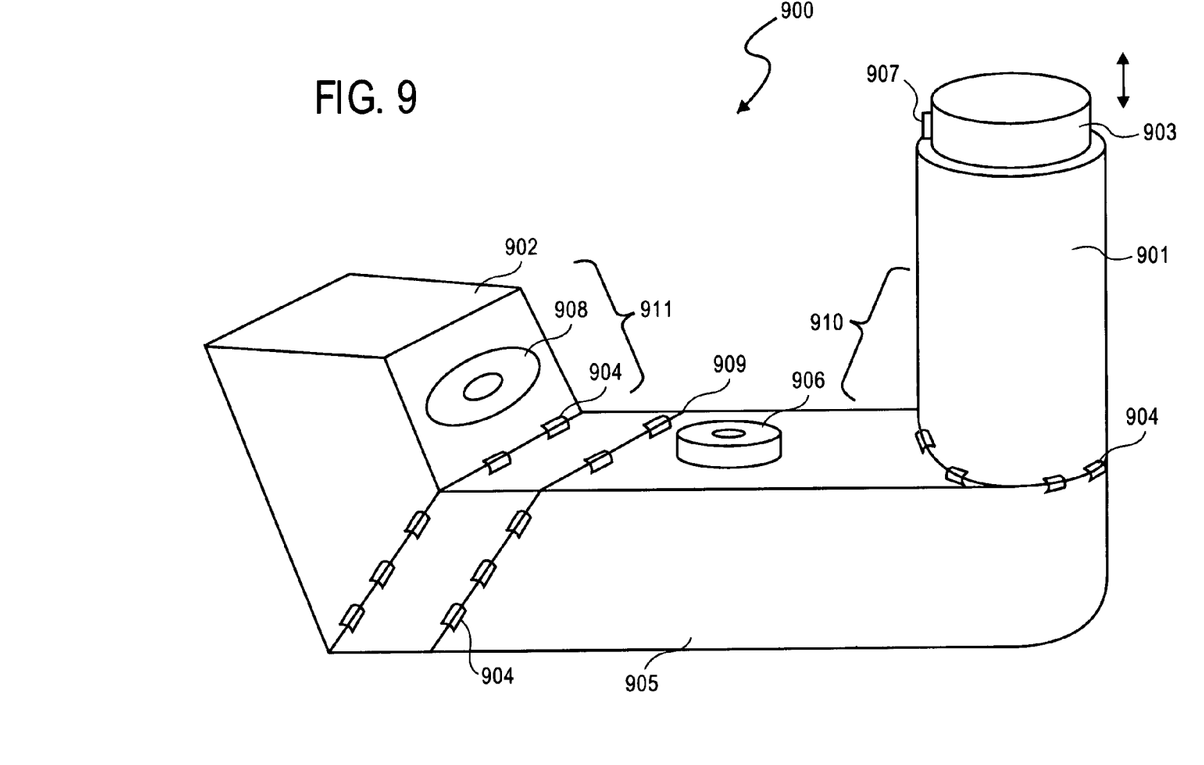
FIG. 9 is an orthogonal view of a portable compact packaged apparatus to measure the size and up to three velocity components with foldable and extendable arms according to one of the embodiments of the invention.

FIG. 9 is an orthogonal view of a portable, extendable compact packaged apparatus 900 to measure the size and up to three velocity components of a spherical object according to one embodiment of the invention. The modular configuration of the apparatus 900 makes it adaptable to various measurement, transportation, and storage conditions. The apparatus 900 has a foldable arm 901 with an output probe light window 907, foldable arm 902 with a receiver window 908, and a base 905 with an output probe window 906. The arms 901 and 902 are connected to a base 905, for example, by hinges 904. When apparatus 900 does not operate, the arms 901 and 902 can be folded toward the base 905 or disconnected from the base 905, for example, for easy transportation and compact storage. In addition, the base 905 is detachable along the line 909 to separate the transmitter section 910 and the receiver section 911. The transmitter section 910 and the receiver section 911 may be incorporated back into a single package by hinges 304. Further, the arm 901 is extendable and has a telescopically movable part 903. The movable part 903 can telescopically slide in and out of the other part of the arm 901 to serve various measurement, transportation, and storage conditions. For an embodiment, the windows 906, 907, and 908 can be telescopically extendable to adjust to various measurement conditions.

Figure 10:
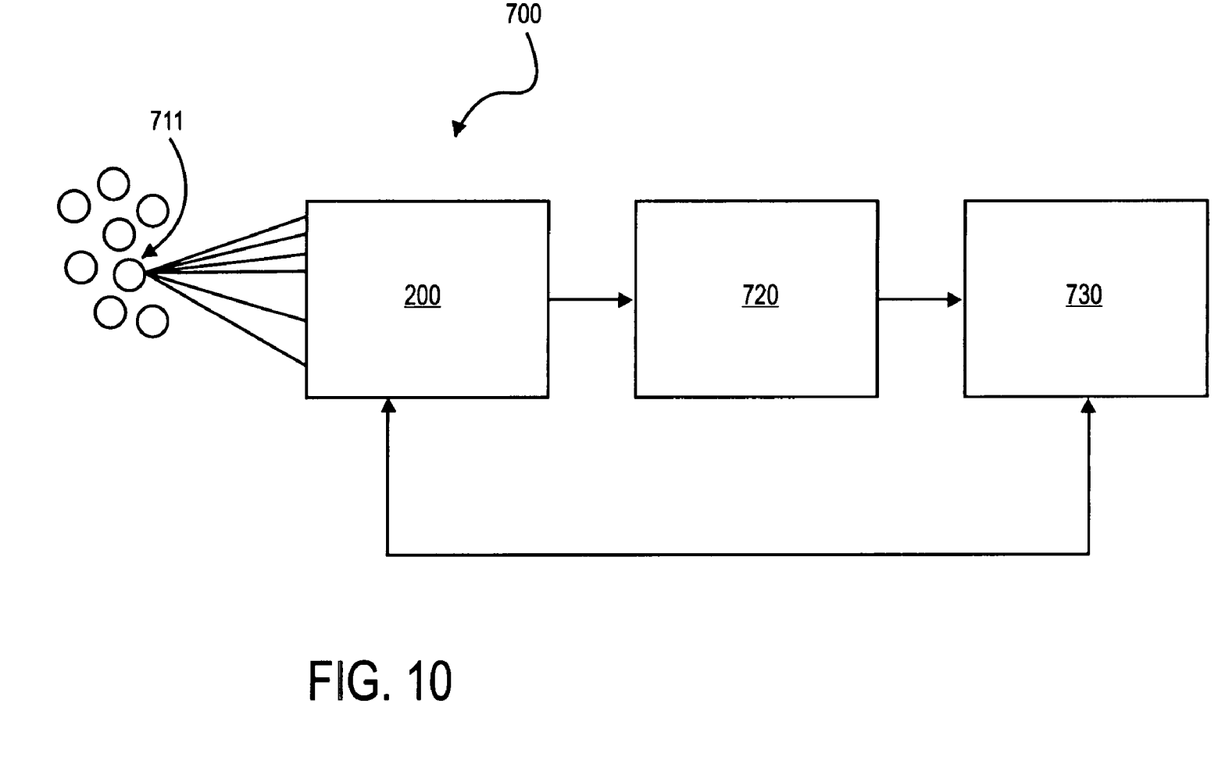
FIG. 10 is a block diagram of a fully-automated system to measure the size and up to three velocity components of a spherical object according to one of the embodiments of the invention.

FIG. 10 is a block diagram of a fully automated system 700 to simultaneously measure the size and three velocity components of a spherical object according to one embodiment of the invention. As shown in FIG. 10, the system 700 includes the compact, apparatus 200 to simultaneously measure the size and up to three velocity components of the spherical objects, a signal processor 720 and a computer 730. The apparatus 200 generates up to three pairs of coherent crossing beams to form a sample volume. Further, the apparatus 200 collects the light scattered from a spherical object 711, for example, from a particle in a spray, to measure the size and up to three velocity components of the spherical object.

For one embodiment, in the apparatus 200, the collected scattered optical signal is sensed and converted to a voltage, pre-amplified, high-pass filtered, further amplified, and then sent to the signal processor 720. For one embodiment, the signal processor 720 includes a Fourier transform based signal processor having an analog and a digital section. Within the analog section of the signal processor, the signal is mixed with a software selectable variable quadrature mixer. The quadrature mixer outputs are low-pass filtered to remove the high frequency and to improve the signal-to-noise ratio. Further, the quadrature outputs of the analog section are sampled and digitized at a software selectable sampling rate in the digital section of the signal processor 720. The digitized signal is then applied to the burst detector. The burst detector output is combined with the analog burst detector output and then used as an input to the adaptive sampling circuitry.

The sampled data for each signal burst is then packed into a single data packet. The data packets are stamped with other relevant information (time of arrival, transit time and external input data) and transferred to the computer 730 via a high-speed PCI interface card for processing using the complex Fourier transform to obtain the signal frequency and phase information.

Computer 730 controls many aspects of the apparatus 200 operation, including, for example, differentiation of a real signal from a false noise spike signal, control of a data rate of the particles within predetermined limits, and assurance that one spherical object is measured at one time. For an embodiment, the computer has a data management system software package installed to control all aspects of the apparatus 200 operation (automated instrument setup and data acquisition, processing, and storage).

In the foregoing specification, the invention has been described with reference to specific exemplary embodiments thereof. It will, however, be evident that various modifications and changes may be made thereto without departing from the broader spirit and scope of the invention. The specification and drawings are, accordingly, to be regarded in an illustrative rather than a restrictive sense.

The invention claimed is:

1. An apparatus comprising:
a compact package having a first portion and a second portion, wherein the first portion has a first opening, and the second portion has a second opening, wherein the first opening is at an angle with respect to the second opening;
a first transmitter inside the compact package to generate a first pair of coherent beams with a substantially high pointing stability, wherein the coherent beams of the first pair are guided by a free space optics inside the package to propagate through space along a first axis and through the first opening in the first portion to cross each other outside the package at a first angle in a first plane to form a sample volume to illuminate a spherical object outside the compact package; and
a receiver inside the compact package to sense through the second opening in the second portion a first light scattered from the spherical object, wherein the receiver comprises three photodetectors to measure a size and a first velocity component of the spherical object.

2. The apparatus of claim 1 further comprising:
a second transmitter inside the compact package to generate a second pair of coherent beams with substantially high pointing stability, wherein the coherent beams of the second pair are guided by the free space optics inside the package to propagate through space along a second axis orthogonal to the first axis and cross each other outside the package at a second angle in a second plane parallel to the first plane to form the sample volume to illuminate a spherical object outside the compact package; and
the receiver inside the compact package further comprises a fourth photodetector to sense a second light scattered from the spherical object to measure a second velocity component that is orthogonal to the first component of the spherical object.

3. The apparatus of claim 2 further comprising:
a third transmitter inside the compact package to generate a third pair of coherent beams with substantially high pointing stability, wherein the coherent beams of the third pair are guided by the free space optics inside the package to propagate through space along a third axis orthogonal to the first axis and parallel to the second axis and cross each other outside the package at a third angle, the third angle is in a third plane orthogonal to the first plane to form the sample volume to illuminate a spherical object outside the package; and
the receiver inside the compact package further comprises a fifth photodetector to sense a third light scattered from the spherical object to measure a third velocity component that is orthogonal to the first and second velocity components of the spherical object.

4. The apparatus of claim 3, wherein the first, second, and third transmitters generate light at a first, a second, and a third wavelength, respectively.

5. The apparatus of claim 3, wherein the first, second, and third transmitters are fiberless.

6. The apparatus of claim 3, wherein the free-space optics inside the package is rigidly aligned.

7. The apparatus of claim 3, wherein each of the transmitters comprises a diode pumped solid-state laser.

8. The apparatus of claim 3 further comprising:
a movable slit aperture strip in front of the receiver to adjust the aperture based on a spherical object arrival rate.

9. The apparatus of claim 8, wherein the movable slit aperture strip is computer controlled.

10. The apparatus of claim 3 further comprising:
a rechargeable battery coupled to the compact package to power the apparatus.

11. An apparatus, comprising:
a compact package having a first portion and a second portion, wherein the first portion has a first opening, and the second portion has a second opening, wherein the first opening is at an angle with respect to the second opening;
a first transmitter inside the compact package to generate a first pair of coherent beams at a first wavelength, wherein the coherent beams of the first pair have substantially high pointing stability and propagate along a first axis through the first opening in the first portion and cross each other outside the compact package at a first angle in a first plane to form a sample volume to illuminate a spherical object;
a receiver inside the compact package to measure through the second opening in the second portion a phase of a first scattered light from the spherical object, the receiver comprises three photodetectors to sense a first scattered light to measure a first velocity component;
a movable computer-controlled slit aperture inside the package in front of the receiver to adjust aperture based on the spherical object arrival rate; and
a real time signal-processing unit inside the package coupled to the receiver to determine the size and a velocity component of the spherical object from the phase of the scattered light.

12. The apparatus of claim 11 further comprising a computer to process data.

13. The apparatus of claim 12, wherein the computer is connected to the signal-processing unit using a wireless link.

14. The apparatus of claim 11, wherein the receiver is placed off-axis from the axis defined by the crossing beams.

15. The apparatus of claim 11 further comprising:
a second transmitter inside the compact package to generate a second pair of coherent beams at a second wavelength with a substantially high pointing stability, wherein the coherent beams of the second pair propagate along a second axis orthogonal to the first axis and cross each other outside the compact package at a second angle in a second plane parallel to the first plane to form the sample volume to illuminate a spherical object; and
the receiver inside the compact package further comprises a fourth photodetector to sense a second light scattered from the spherical object to measure a second velocity component that is orthogonal to the first velocity component of the spherical object.

16. The apparatus of claim 15 further comprising:
a third transmitter inside the compact package to generate a third pair of coherent beams at a third wavelength with substantially high pointing stability, the coherent beams of the third pair propagate along a third axis orthogonal to the first axis and parallel to the second axis and cross each other outside the compact package at a third angle, the third angle is in a third plane orthogonal to the first plane to form the sample volume to illuminate a spherical object; and
the receiver inside the compact package further comprises a fifth photodetector to sense a third light scattered from the spherical object to measure a third velocity component that is orthogonal to the first and second velocity components of the spherical object.

17. The apparatus of claim 16, wherein each of the transmitters comprises a diode pumped solid-state laser.

18. A system comprising:
a compact package having a first portion and a second portion, wherein the first portion has a first opening, and the second portion has a second opening, wherein the first opening is at an angle with respect to the second opening;
a first laser inside the compact package to generate a first pair of substantially stable coherent beams at a first wavelength;
a first free-space optics inside the compact package coupled to the first laser to guide the coherent beams through the first opening in the first portion in such a way that the coherent beams cross each other outside the compact package at a first angle to form a sample volume to illuminate a spherical object;
a first frequency modulator coupled to the first laser and to the first free-space optics to modulate one of the coherent beams;
a collecting optics inside the compact package to collect a light scattered from the spherical object;
three spaced apart photodetectors inside the compact package coupled to the collecting optics to sense the scattered light collected by the collecting optics through the second opening in the second portion;
a phase measurement unit coupled to the three photodetectors to measure the phase of the scattered light, wherein the first laser, the first free-space optics, the first frequency modulator, the collecting optics, the three spaced apart photodetectors, and the phase measurement unit are inside the compact package; and
a signal-processing unit coupled to the phase detector unit to determine a size and a first velocity component of the spherical object.

19. The system of claim 18 further comprising:
a second laser to generate a second pair of substantially stable coherent beams at a second wavelength;
a second free-space optics to guide the coherent beams in such a way that the coherent beams cross each other outside the compact package at a second angle to form the sample volume to illuminate the spherical object;
a second frequency modulator inside the package coupled to the second laser to modulate one of the coherent beams of the second pair; and
a fourth photodetector coupled to the collecting optics and to the phase measurement unit to sense the second scattered light, wherein the second laser, the second free-space optics, the second frequency modulator, the collecting optics, and the fourth photodetector are inside the compact package.

20. The system of claim 19 further comprising:
a third laser to generate a third pair of substantially stable coherent beams at a third wavelength;
a third free-space optics to guide the coherent beams in such a way that the coherent beams cross each other outside the compact package at a third angle to form the sample volume to illuminate the spherical object;
a third frequency modulator inside the package coupled to the third laser to modulate one of the coherent beams of the third pair; and
a fifth photodetector coupled to the collecting optics and to the phase measurement unit to sense the third scattered light, wherein the third laser, the third free-space optics, the third frequency modulator, and the fifth photodetector are inside the compact package.

21. The system of claim 20, wherein the first, the second, and the third lasers are a first, a second, and a third diode pumped solid-state laser.

* * * * *